(12) United States Patent
Avnery

(10) Patent No.: US 6,738,451 B2
(45) Date of Patent: May 18, 2004

(54) X-RAY IRRADIATION APPARATUS

(75) Inventor: Tzvi Avnery, Winchester, MA (US)

(73) Assignee: Advanced Electron Beams, Inc., Wilmington, MA (US)

(*) Notice: Subject to any disclaimer, the term of this patent is extended or adjusted under 35 U.S.C. 154(b) by 0 days.

(21) Appl. No.: 10/102,509

(22) Filed: Mar. 19, 2002

(65) Prior Publication Data

US 2002/0154740 A1 Oct. 24, 2002

Related U.S. Application Data

(60) Provisional application No. 60/277,322, filed on Mar. 20, 2001.

(51) Int. Cl.[7] .................................. G21K 5/00
(52) U.S. Cl. ..................... 378/64; 378/69; 378/140; 378/143
(58) Field of Search ............... 378/64–69, 140, 378/143

(56) References Cited

U.S. PATENT DOCUMENTS

| | | | | |
|---|---|---|---|---|
| 4,029,967 A | 6/1977 | Tetzlaff | ................. | 250/492 R |
| 4,159,437 A | 6/1979 | Sahores | ................. | 313/59 |
| 4,274,005 A | * | 6/1981 | Yamamura et al. | ............ 378/9 |
| 4,292,563 A | 9/1981 | Gabbay et al. | ................. | 313/56 |
| 4,484,341 A | 11/1984 | Luniewski | ................. | 378/69 |
| 4,646,338 A | 2/1987 | Skillicorn | ................. | 378/110 |
| 5,577,090 A | * | 11/1996 | Moses | ............ 378/64 |
| 6,195,411 B1 | 2/2001 | Dinsmore | ................. | 378/65 |
| 6,463,123 B1 | * | 10/2002 | Korenev | ............ 378/69 |

FOREIGN PATENT DOCUMENTS

| | | | | |
|---|---|---|---|---|
| EP | 0 275 592 A1 | 7/1988 | ............ | H01J/35/06 |
| EP | 0 553 912 A1 | 8/1993 | ............ | H01J/35/18 |
| GB | 2 281 812 A | 3/1995 | ............ | H01J/3/14 |
| JP | 58108637 | 6/1983 | ............ | H01J/35/08 |
| JP | 10039100 | 2/1998 | ............ | G21K/5/08 |
| WO | WO 98/50937 | 11/1998 | ............ | H01J/35/14 |

OTHER PUBLICATIONS

Kuroda, K., et al., "Efficient Extraction Window for High–Throughput X–Ray Lithography Beamlines," *Rev. of Sci. Instrum., Proc. of the 5th Internat'l Conf. on Synchrotron Radiation Instrum.*, 66 (2) : 2151–2153 (1995).

* cited by examiner

*Primary Examiner*—Craig E. Church
(74) *Attorney, Agent, or Firm*—Hamilton, Brook, Smith & Reynolds, P.C.

(57) ABSTRACT

An X-ray beam emitter including a vacuum chamber having a target window. An electron generator is positioned within the vacuum chamber for generating electrons that are directed at the target window for forming X-rays. The X-rays pass through the target window in an X-ray beam.

34 Claims, 5 Drawing Sheets

X-RAY IRRADIATION APPARATUS

RELATED APPLICATION

This application claims the benefit of U.S. Provisional Application No. 60/277,322 filed on Mar. 20, 2001. The entire teachings of the above application are incorporated herein by reference.

BACKGROUND

Many medical instruments are reusable and require sterilization between uses. Some of these instruments, for example, endoscopes and gastroscopes, are difficult to fully sterilize. Typically, such instruments are sterilized by hydrogen peroxide which is flushed through the interior as well as over the exterior of the instruments. This is not only a time consuming process, taking about one hour, but often the instruments have contaminated areas which the sterilizing process cannot sufficiently penetrate to fully sterilize such as biofilms of bacteria. In addition, the hydrogen peroxide is not able to kill all viruses. Another common sterilization agent is ethylene oxide which produces similar results. Other methods of sterilization include irradiation with gamma radiation, but this method can take up to 24 hours with current equipment.

SUMMARY

The present invention includes an apparatus that can be employed for sterilizing articles such as medical instruments more quickly and thoroughly than current methods. The present invention includes an X-ray beam emitter having vacuum chamber with a target window. An electron generator is positioned within the vacuum chamber for generating electrons that are directed at the target window for forming X-rays. The X-rays pass through the target window in an X-ray beam.

In particular embodiments, the target window has a thickness which substantially prevents the passage of electrons therethrough. The electrons and X-ray beam travel in substantially the same direction. The X-ray beam is directed into an irradiation region for irradiating articles positioned therein. In some embodiments, the emitter is a sterilization device where articles irradiated by the X-ray beam are sterilized.

The X-ray beam emitter can be part of an X-ray beam system in an X-ray irradiation apparatus which includes at least one X-ray beam emitter for directing at least one X-ray beam into an irradiation region. In particular embodiments, the X-ray beam system includes more than one X-ray beam emitter for directing X-ray beams into the irradiation region from different directions. In one embodiment, at least three X-ray beam emitters are positioned around the irradiation region thereby forming a central irradiation chamber. In another embodiment, six X-ray beam emitters are positioned in a ring around the irradiation region and abut against each other. The X-ray beam system may include more than one ring of X-ray beam emitters which are joined together. In some embodiments, the apparatus is a sterilization apparatus where articles are positioned within the irradiation chamber for sterilization.

The present invention also includes a method of forming X-rays. The method includes providing a vacuum chamber having a target window. An electron generator is positioned within the vacuum chamber for generating electrons. The electrons are directed at the target window to form X-rays which pass through the target window in an X-ray beam. The target window has a thickness which substantially prevents the passage of electrons therethrough. The electrons and the X-ray beam travel in substantially the same direction.

When employed for sterilization purposes, the X-ray beams generated by embodiments of the present invention are able to deeply penetrate into the articles being irradiated. Both surface and imbedded contaminants are able to be irradiated for relatively quick and thorough sterilization in comparison to traditional methods.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
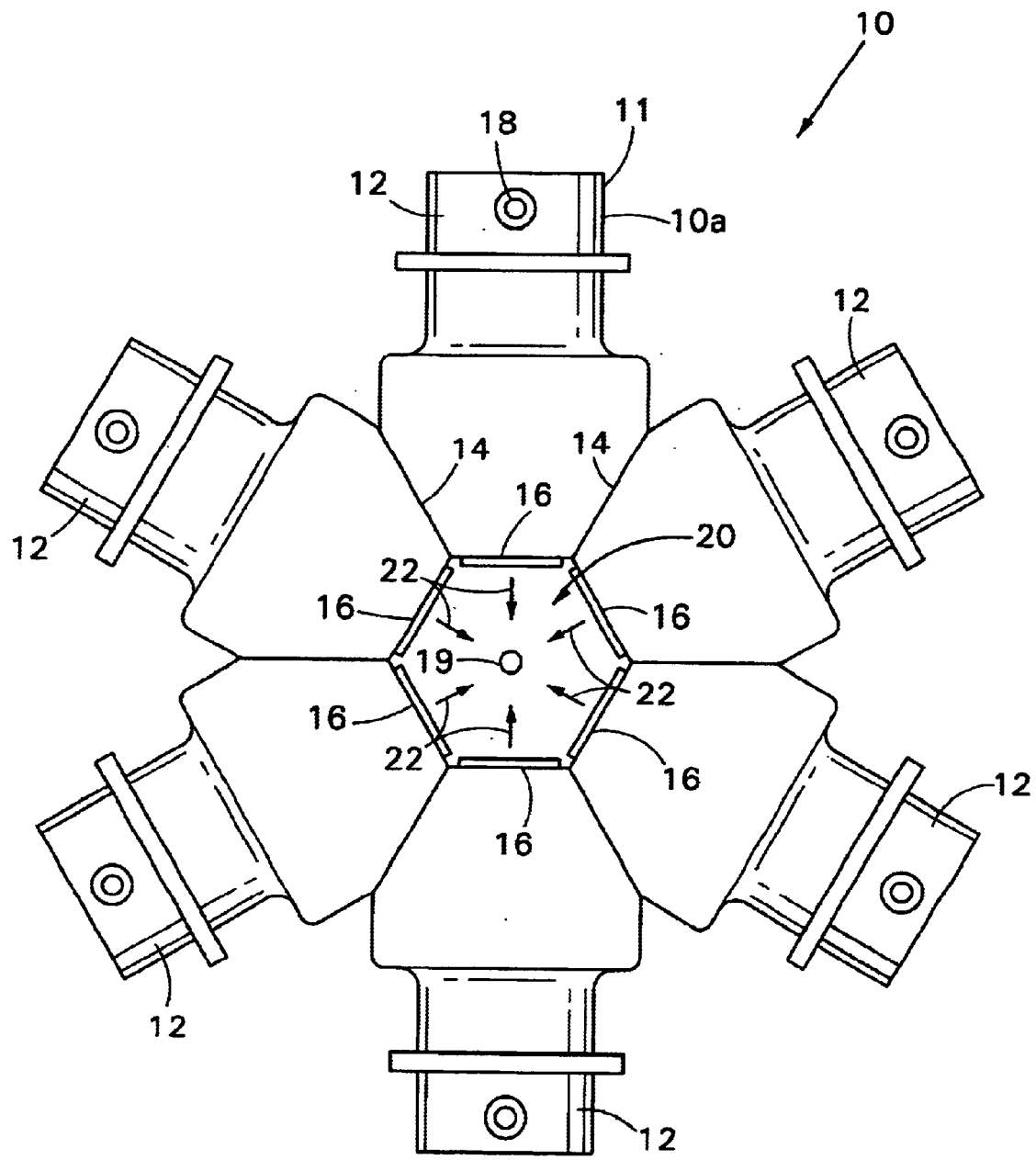
FIG. 1 is a simplified end view of an embodiment of the present invention X-ray beam irradiation apparatus.
Figure 2:
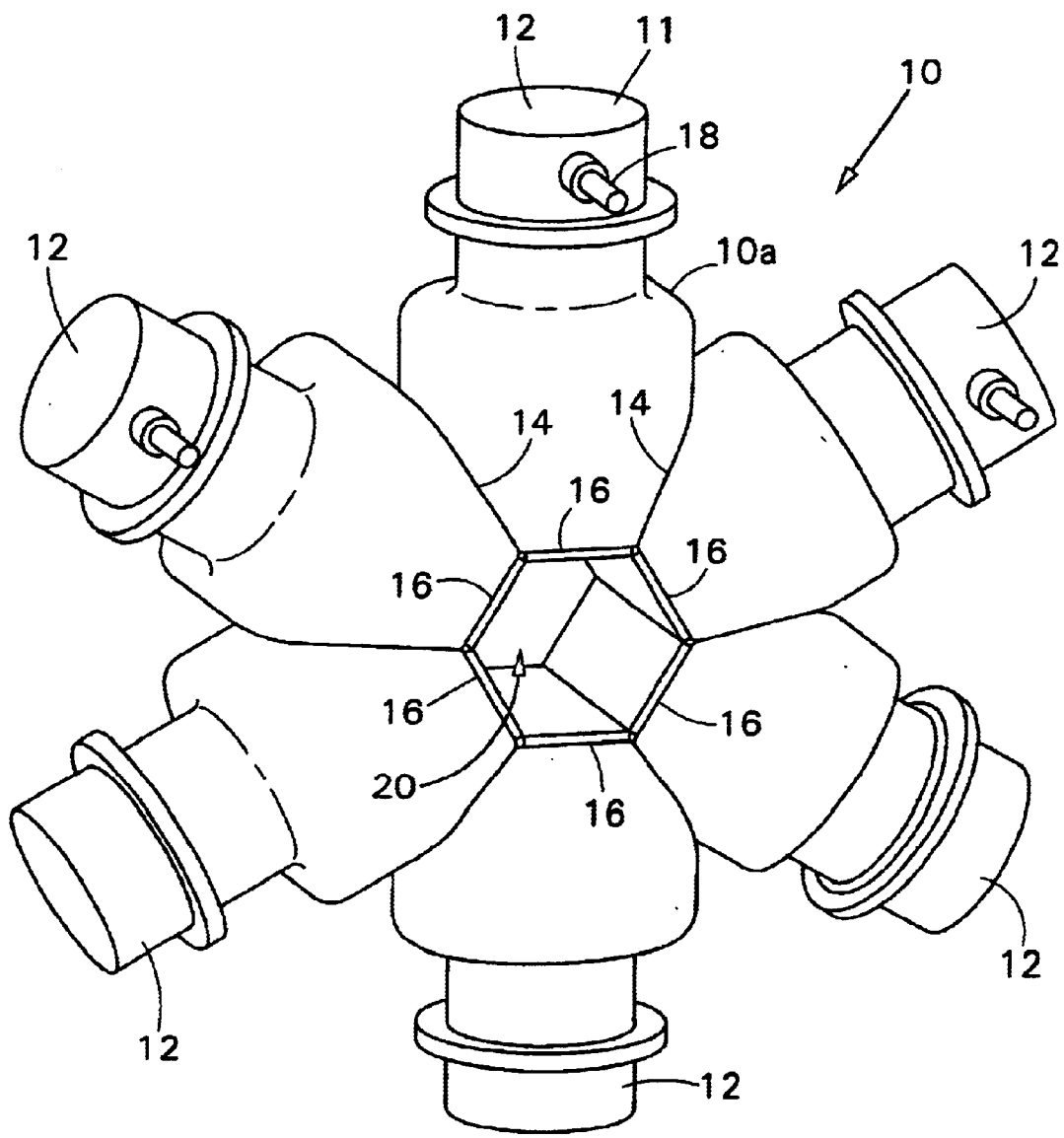
FIG. 2 is a simplified perspective view of the X-ray beam irradiation apparatus of FIG. 1.

Referring to FIGS. 1 and 2, X-ray beam irradiation apparatus 10 is suitable for sterilizing objects or articles, for example, medical instruments, tools or components. In the embodiment depicted in FIGS. 1 and 2, X-ray beam irradiation apparatus 10 includes an x-ray beam system having an X-ray irradiation unit 11 for irradiating articles 19. The X-ray irradiation unit 11 of the embodiment depicted in FIGS. 1 and 2 includes a series of X-ray beam emitters 12 each having a target window 16 through which an X-ray beam 22 is generated. The X-ray beam emitters 12 have angled side walls 14 which allow the X-ray beam emitters 12 to be abutted against each other and joined together in a ring 10a surrounding an irradiation region or chamber 20 so that the X-ray beam emitters 12 can direct the X-ray beams 22 radially inwardly into irradiation chamber 20 from different directions. FIGS. 1 and 2 depict six X-ray beam emitters 12 abutted against each other to form a hexagonal shaped irradiation chamber 20. The target windows 16 are closely positioned to each other so that the X-ray beams 22 directed into irradiation chamber 20 combine to provide substantially continuous radially inward X-ray beam coverage.

In use, articles 19 (FIG. 1) such as medical instruments requiring sterilization are typically positioned within irradiation chamber 20. Doors, such as those shown in FIG. 3, designated by reference numeral 26, may be employed on opposite ends of irradiation chamber 20 to provide shielding of the X-rays. Alternatively, elongated entrance and exit tunnels can be employed to provide shielding. Power to the X-ray beam emitters 12 is then provided so that X-ray beams 22 are directed inwardly into irradiation chamber 20. The X-ray beams 22 are able to disable, damage or kill bacteria, viruses, and organisms on the surface of the article 19. In addition, the X-ray beams 22 can penetrate into the article 19 to sterilize regions deep within the article 19 as well as penetrate and sterilize thick layers or regions of contamination. Instruments such as an endoscope may require a sterilization time of about a half hour at a low power of 5 kW per emitter 12 to achieve thorough sterilization. This is about half the time in comparison to the one hour typically required when sterilizing with hydrogen peroxide. Even over such an amount of time, instruments sterilized by hydrogen peroxide are not as thoroughly sterilized as in the present invention.

Although six X-ray beam emitters 12 are shown in FIGS. 1 and 2 to form X-ray irradiation unit 11, it is understood that any number of X-ray beam emitters 12 can be employed. When three emitters 12 are employed, irradiation chamber 20 can be triangular in shape, with four emitters 12, square, and with five and above, polygonal. When multiple emitters 12 are employed, irradiation chamber 20 can also have configurations that are wide and flat, or convoluted, depending upon the situation. In some cases, X-ray irradiation unit 11 may only need one or two X-ray beam emitters 12. In such cases, reflectors for reflecting X-rays can be used in combination with the X-ray beam emitters 12. Additionally, although x-ray emitters 12 have been shown to be joined together in a ring 10a, alternatively, one or more X-ray emitters 12 may be positioned for providing X-ray beams that are not in a substantially continuous circle, for example, from one or two directions. When two X-ray beam emitters 12 are employed, the emitters 12 can be arranged in opposed fashion.

Figure 3:
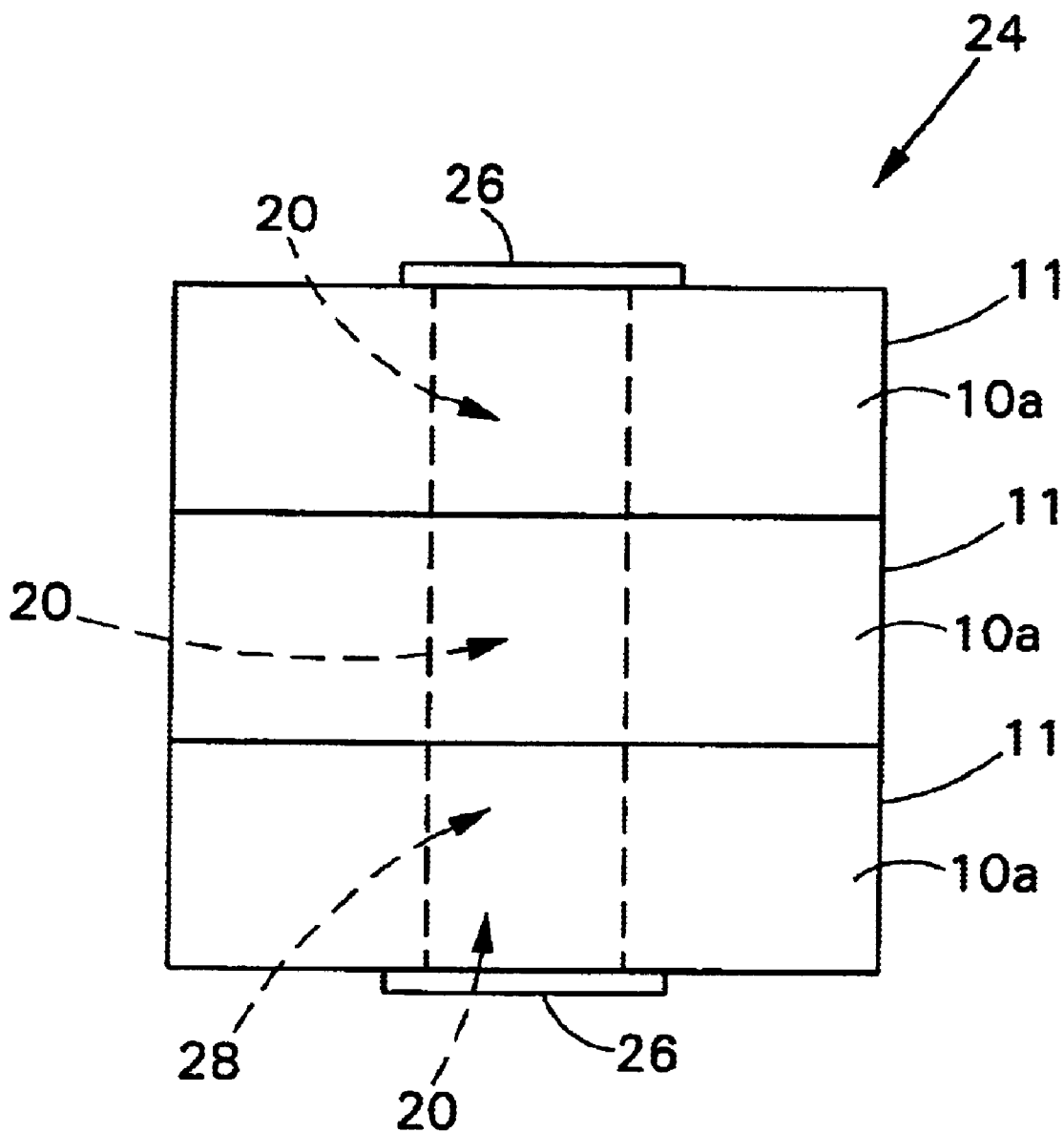
FIG. 3 is a side view of another embodiment of the present invention X-ray beam irradiation apparatus.

Referring to FIG. 3, X-ray beam irradiation apparatus 24 is employed when sterilizing articles 19 that are too long to fit within apparatus 10. X-ray beam irradiation apparatus 24 includes an X-ray beam system having more than one X-ray irradiation unit 11 joined together. In one embodiment, each X-ray irradiation unit 11 includes a ring 10a of X-ray beam emitters 12 similar to that depicted in FIGS. 1 and 2. The rings 10a are abutted against each other and joined together so that the irradiation chambers 20 of each ring 10a join together collectively to form one long irradiation region or chamber 28. Three X-ray irradiation units 11 are shown abutted together, however, less than three or more than three units 11 can be joined together. Typically, X-ray beam irradiation apparatus 24 includes doors 26 to provide shielding of the X-rays. Although instruments are typically positioned in a stationary manner within irradiation chamber 28, alternatively, a conveyor system can be employed to slowly move articles 19 through irradiation chamber 28. The conveyor system may include conveyor belts and/or rollers. When a conveyor system is employed, entrance and exit tunnels may be desirable to provide shielding.

It is understood that X-ray irradiation apparatus 24 can have X-ray irradiation units 11 of configurations that are different than ring 10a such as discussed above. In addition, some embodiments of the irradiation units 11 can include mechanisms for moving one or more emitters 12 over or around an article 19 for providing X-ray irradiation with a minimum number of emitters 12. In one embodiment, a ring 10a is translated longitudinally along article 19. In another embodiment, an emitter 12 is rotated around article 19 and can also be translated longitudinally over article 19. In configurations where an emitter 12 is rotated around article 19, employing more than one emitter 12 can reduce the amount of rotation required. For example, if two emitters 12 are employed positioned in opposed fashion, the emitters 12 can be rotated only 180° around article 19.

In addition to sterilizing medical instruments, tools or components, X-ray beam irradiation apparatuses 10 and 24 can be employed to sterilize implantable devices or components such as artificial joints, pins, plates, pumps, pacemakers, etc. Furthermore, a wide variety of objects or articles 19 can be sterilized, including items for use in a sterile room or environment. In some instances, it may be desirable to sterilize substances such as powders, liquids or food items. Referring to FIG. 3, X-ray beam irradiation apparatus 24 can be employed as a sterilizing entrance for articles 19 entering a sterile environment where one end of apparatus 24 is connected to the sterile environment, typically, extending through a wall thereof. One door 26 allows articles 19 to be inserted into apparatus 24 from the exterior for sterilization. The other door 26 allows removal of the sterilized article 19 from apparatus 24 into the sterile environment.

Figure 4:
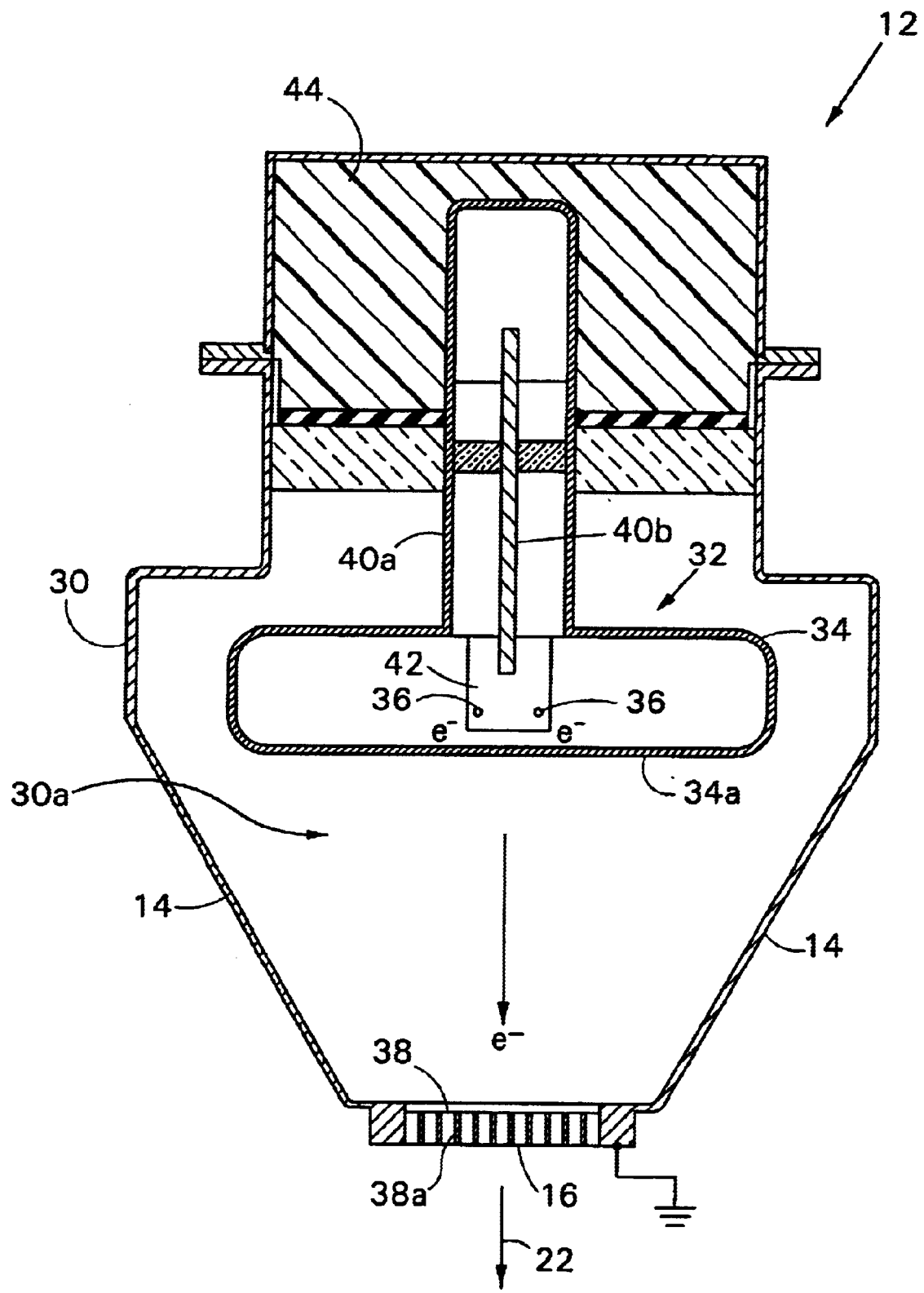
FIG. 4 is an end sectional view of an embodiment of an X-ray beam emitter in accordance with the present invention.
Figure 5:
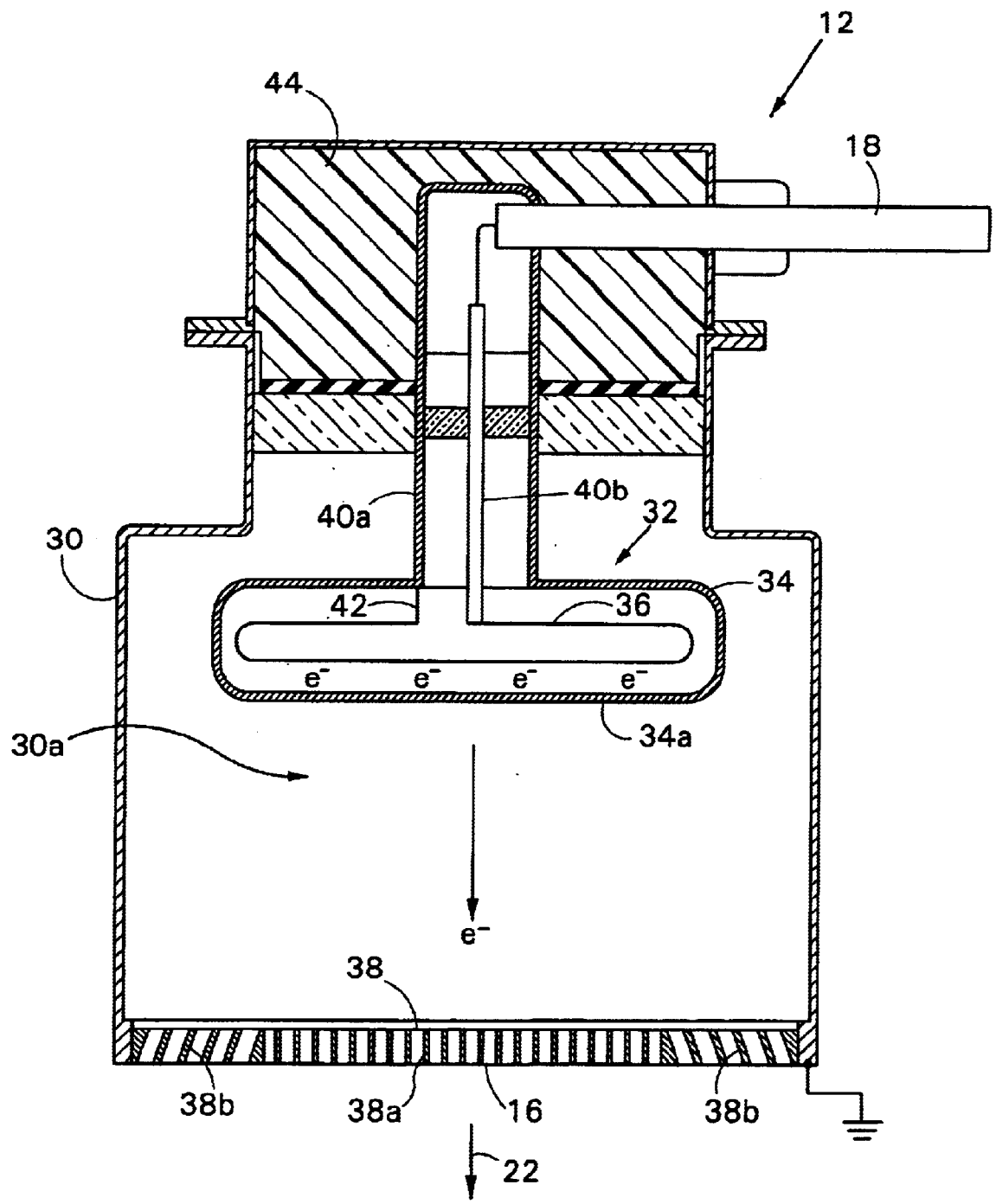
FIG. 5 is a side sectional view of the X-ray beam emitter of FIG. 4.

Referring to FIGS. 4 and 5, X-ray beam emitter 12 in one embodiment includes a hermetically sealed vacuum chamber 30 having a rectangular target window 16 positioned at one end thereof. An electron generator 32 is positioned within the interior 30a of vacuum chamber 30 for generating electrons $e^-$ which are accelerated towards the target window 16 for forming X-rays. The target window 16 typically consists of a thin metallic foil that has a thickness sufficient to substantially prevent the passage of electrons $e^-$ through while allowing passage of X-rays. The target window 16 is supported by a support plate 38 having a series of holes 38a therethrough which allow the electrons $e^-$ to reach target window 16. In some embodiments, outwardly angled holes 38b may be included at the far ends of support plate 38 (FIG. 5) to direct more electrons $e^-$ to the ends of target window 16. The target window 16 is sealed to support plate 38 by bonding under heat and pressure, but alternatively could be brazed or welded. In one embodiment, the target window 16 can be 12 inches long so that irradiation chamber 20 is about 12 inches long. When X-ray beam emitters 12 are to be abutted against each other in a ring such as ring 10a (FIG. 1), the emitters 12 can have angled sides 14 which extend towards and near the longer sides of the target window 16 (FIG. 4). Sides 14 are angled at about 60° when six emitters 12 are abutted together, however, the angle of sides 14 can differ depending upon the number of emitters 12 joined together. In some irradiation chamber 20 configurations, the angled sides 14 can be omitted, for example, in some rectangular configurations. A tube may be extended from vacuum chamber 30 and connected to a vacuum pump for evacuating vacuum chamber 30 which is then sealed off to hermetically seal vacuum chamber 30.

The electron generator 32 has a filament housing 34 which in one embodiment is disc shaped and has a series of openings in the bottom 34a. Tungsten filaments 36 are positioned within housing 34 for generating the electrons $e^-$. Filament housing 34 is electrically connected to a high voltage supply by tubular conductor 40a and cable 18. Common ranges are 100–300 kV with 125 kV being typical. In some applications, voltages 100 kV and above 300 kV may be desirable. Target window 16 is electrically grounded to impose a high voltage potential between filament housing 34 and target window 16. Filaments 36 are provided power by a filament power supply electrically connected to cable 18 and are electrically connected at one end to a conductor 42 extending within the interior of filament housing 34, and are electrically connected at the other end to a conductor 40b extending from cable 18. The upper portions of conductor 40a is embedded within insulating materials 44.

In use, the filaments 36 are provided with power to heat filaments 36 to about 3400° F. to 4200° F. which causes free electrons $e^-$ to form on filaments 36. The high voltage potential imposed between the filament housing 34 and target window 16 causes the free electrons e⁻ on filaments 36 to accelerate from the filaments 36 in a beam through openings in the bottom 34a of filament housing 34 to target window 16. The target window 16 is typically a thin foil of gold, titanium or tungsten about 3 microns thick which substantially blocks or prevents the passage of electrons e⁻ therethrough, but, alternatively, may be formed of titanium with a layer of gold thereon, or be formed of gold with copper or silver. Typically, metals with a high Z number and good thermal conductivity are preferred, but it is understood that the material of target window 16 can vary depending upon the application at hand. For example, materials and combinations other than those described above can be used. The electrons e⁻ striking the target window 16 typically do not pass through but instead form X-rays which exit or emerge from the target window 16 in an X-ray beam 22 and continue to travel substantially in the same forward direction as the electrons e⁻ were traveling. In other words, the beam of electrons e⁻ is transformed or changed by target window 16 into the X-ray beam 22 resulting in a continuous two-part or stage beam where the first stage is formed by the beam of electrons e⁻ and the second stage is formed by the X-ray beam 22. The X-ray beam 22 exits target window 16 with substantially the same outline as target window 16. The production of X-rays in this manner provides a relatively efficient broad X-ray beam 22 because both the electrons e⁻ and the X-ray beam 22 are traveling in the same forward direction. The beam of electrons e⁻ and the X-ray beam 22 are shown to be perpendicular or substantially perpendicular to target window 16. In some situations, electrons e⁻ might strike target window 16 at an angle.

In some embodiments, target window 16 may be configured to allow some electrons e⁻ to pass through to provide a mix of electrons e⁻ and X-rays. In further embodiments, the target window 16 can be replaced by an electron beam exit window which allows the electrons e⁻ to exit the emitters 12 in an electron beam. In such a case, the electrons e⁻ strike the surface of the article to be sterilized thereby sterilizing the surface and, at the same time, creating X-rays which sterilize the interior. Such an embodiment can be used to sterilize or decontaminate any type of suitable equipment. The target window 16 can be configured to suit particular arrangements, and can be of shapes other than rectangular.

While this invention has been particularly shown and described with references to preferred embodiments thereof, it will be understood by those skilled in the art that various changes in form and details may be made therein without departing from the scope of the invention encompassed by the appended claims. For example, features of the various embodiments discussed above may be combined with each other or omitted. It is understood that the configuration, shape, dimensions, size and power of X-ray emitter 12 can be varied depending upon the application at hand as well as the shape of the target window 16. Multiple emitters 12 may be positioned side by side for generating an X-ray beam 22 from one direction, or positioned in opposing directions for generating X-ray beams 22 from two directions. In some configurations, the X-ray beams 22 from emitters 12 are not joined in a continuous manner. In addition, X-ray emitters 12 and apparatuses 10 and 24 may be employed to sterilize any desired article, or may be used for other typical purposes, such as taking an X-ray of a patient or curing coatings.

What is claimed is:

1. An X-ray beam emitter comprising:
    a vacuum chamber having a target window; and
    an electron generator positioned within the vacuum chamber for generating electrons that are directed at the target window for forming X-rays which pass through the target window in an X-ray beam, the target window being supported by a support plate having a series of holes therethrough which allow passage of the electrons therethrough to reach the target window.

2. The emitter of claim 1 in which the target window has a thickness which substantially prevents the passage of electrons therethrough.

3. The emitter of claim 2 in which the electrons and X-ray beam travel in substantially the same direction.

4. The emitter of claim 3 further comprising an irradiation region into which the X-ray beam is directed for irradiating articles.

5. The emitter of claim 4 in which the emitter is a sterilization device where articles irradiated by the X-ray beam are sterilized.

6. An X-ray irradiation apparatus comprising:
    an X-ray beam system for directing at least one X-ray beam into an irradiation region, the X-ray beam system comprising at least one X-ray beam emitter, said X-ray beam emitter comprising:
        a vacuum chamber having a target window; and
        an electron generator positioned within the vacuum chamber for generating electrons that are directed at the target window for forming X-rays which pass through the target window as said X-ray beam, the target window being supported by a support plate having a series of holes therethrough which allow passage of the electrons therethrough to reach the target window.

7. The apparatus of claim 6 in which the target window of the X-ray beam emitter has a thickness which substantially prevents the passage of electrons therethrough.

8. The apparatus of claim 7 in which the electrons and X-ray beam travel in substantially the same direction.

9. The apparatus of claim 8 in which the X-ray beam system comprises more than one X-ray beam emitter for directing X-ray beams into the irradiation region from different directions.

10. The apparatus of claim 8 in which the X-ray beam system comprises at least three X-ray beam emitters positioned in a ring around the irradiation region, thereby forming a central irradiation chamber.

11. The apparatus of claim 9 in which the X-ray beam system comprises six X-ray beam emitters positioned in a ring around the irradiation region and abutting each other.

12. The apparatus of claim 10 in which the X-ray beam system comprises more than one ring of X-ray beam emitters joined together.

13. The apparatus of claim 8 in which the apparatus is a sterilization apparatus where articles are positioned within the irradiation chamber for sterilization.

14. The apparatus of claim 8 in which the X-ray beam system comprises at least one irradiation unit having at least one X-ray beam emitter.

15. The apparatus of claim 14 in which the X-ray beam system comprises more than one irradiation unit joined together.

16. An X-ray sterilization apparatus comprising:
    an X-ray beam system for directing at least one X-ray beam into an irradiation region, the X-ray beam system comprising at least one X-ray beam emitter, said X-ray beam emitter comprising:

a vacuum chamber having a target window; and an electron generator positioned within the vacuum chamber for generating electrons that are directed at the target window for forming X-rays which pass through the target window as said X-ray beam, said X-ray beam for sterilizing articles positioned within the irradiation zone, the target window being supported by a support plate having a series of holes therethrough which allow passage of the electrons therethrough to reach the target window.

17. A method of forming an X-ray beam emitter comprising:

providing a vacuum chamber having a target window; and positioning an electron generator within the vacuum chamber for generating electrons that are directed at the target window for forming X-rays which pass through the target window in an X-ray beam, the target window being supported by a support plate having a series of holes therethrough which allow passage of the electrons therethrough to reach the target window.

18. The method of claim 17 further comprising providing the target window with a thickness which substantially prevents the passage of electrons therethrough.

19. The method of claim 18 further comprising configuring the X-ray beam emitter so that the electrons and X-ray beam travel in substantially the same direction.

20. The method of claim 19 further comprising forming an irradiation region into which the X-ray beam is directed for irradiating articles.

21. A method of forming an X-ray irradiation apparatus comprising:

forming an X-ray beam system for directing at least one X-ray beam into an irradiation region, the X-ray beam system comprising at least one X-ray beam emitter; and providing the X-ray beam emitter with a vacuum chamber having a target window, and an electron generator positioned within the vacuum chamber for generating electrons that are directed at the target window for forming X-rays which pass through the target window as said X-ray beam, the target window being supported by a support plate having a series of holes therethrough which allow passage of the electrons therethrough to reach the target window.

22. The method of claim 21 further comprising providing the target window with a thickness which substantially prevents the passage of electrons therethrough.

23. The method of claim 22 further comprising configuring the X-ray beam emitter so that the electrons and X-ray beam travel in substantially the same direction.

24. The method of claim 23 further comprising providing the X-ray beam system with more than one X-ray beam emitter for directing X-ray beams into the irradiation region from different directions.

25. The method of claim 23 further comprising providing the X-ray beam system with at least three X-ray beam emitters positioned in a ring around the irradiation region, thereby forming a central irradiation chamber.

26. The method of claim 25 further comprising positioning six X-ray beam emitters in a ring around the irradiation region and abutting each other.

27. The method of claim 25 further comprising forming the X-ray beam system from more than one ring of X-ray beam emitters joined together.

28. The method of claim 23 further comprising providing the X-ray beam system with at least one irradiation unit having at least one X-ray beam emitter.

29. The method of claim 28 further comprising joining more than one irradiation unit together to form the X-ray beam system.

30. The method of claim 22 further comprising forming the apparatus into a sterilization apparatus for sterilizing articles positioned within the irradiation region.

31. A method of forming an X-ray sterilization apparatus comprising:

forming an X-ray beam system for directing at least one X-ray beam into an irradiation region, the X-ray beam system comprising at least one X-ray beam emitter; and providing the X-ray beam emitter with a vacuum chamber having a target window, and an electron generator positioned within the vacuum chamber for generating electrons that are directed at the target window for forming X-rays which pass through the target window as said X-ray beam, said X-ray beam for sterilizing articles positioned within the irradiation zone, the target window being supported by a support plate having a series of holes therethrough which allow passage of the electrons therethrough to reach the target window.

32. A method of forming X-rays comprising:

providing a vacuum chamber having a target window;

positioning an electron generator within the vacuum chamber for generating electrons; and directing the electrons at the target window to form X-rays which pass through the target window in an X-ray beam, the target window being supported by a support plate having a series of holes therethrough which allow passage of the electrons therethrough to reach the target window.

33. The method of claim 32 further comprising providing the target window with a thickness which substantially prevents the passage of electrons therethrough.

34. The method of claim 33 further comprising configuring the X-ray beam emitter so that the electrons and X-ray beam travel in substantially the same direction.

* * * * *